Figure 7:
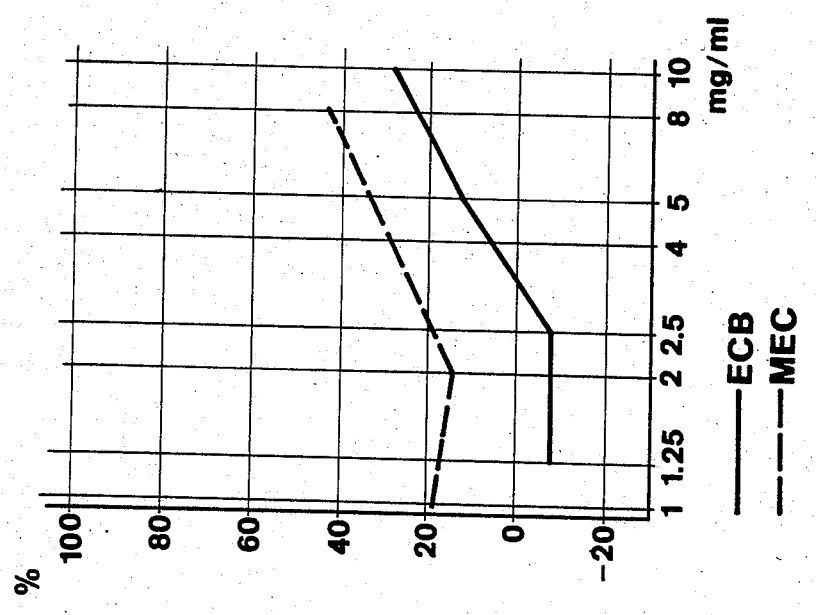

United States Patent [19]

Tubaro et al.

[11] Patent Number: 4,584,198

[45] Date of Patent: Apr. 22, 1986

[54] THERAPEUTIC COMPOSITIONS HAVING ANTIBACTERIC ACTIVITY COMPRISING A FRACTION EXTRACTED FROM CAMOMILE FLOWERS AND PROCESS FOR THE PREPARATION OF SAID FRACTION

[75] Inventors: Aurelia Tubaro, Gorizia; Roberto Della Loggia, Trieste; Elena Banfi, Trieste; Marina Cinco, Trieste; Claudio Redaelli, Perego, all of Italy

[73] Assignee: Bonomelli S.p.A., Dolzago, Italy

[21] Appl. No.: 499,894

[22] Filed: Jun. 1, 1983

[30] Foreign Application Priority Data

Jun. 2, 1982 [IT] Italy ............................... 21659 A/82

[51] Int. Cl.$^4$ ............................................. A61K 35/78
[52] U.S. Cl. .................................................. 424/195.1
[58] Field of Search ............................. 424/195, 195.1

[56] References Cited

U.S. PATENT DOCUMENTS 1,926,929  9/1933  Abelmann ........................... 424/195

FOREIGN PATENT DOCUMENTS

| 0096016 | 12/1983 | European Pat. Off. | 424/195 |
|---|---|---|---|
| 384134 | 10/1923 | Fed. Rep. of Germany | 424/195 |
| 609884 | 2/1935 | Fed. Rep. of Germany | 424/195 |
| 936592 | 1/1956 | Fed. Rep. of Germany | 424/195 |
| 1015120 | 4/1952 | France | 424/195 |
| 2165856 | 8/1973 | France | 424/195 |
| 2187381 | 1/1974 | France | 424/195 |
| 2303526 | 10/1976 | France | 424/195 |

OTHER PUBLICATIONS

Chem. Absts., 92: 191892z, 1980.
Chemical Abstracts, vol. 95, 1981, p. 246.
Chemical Abstracts, vol. 79, 1978, p. 292.
Biological Abstracts, vol. 55, p. 35976.

*Primary Examiner*—Albert T. Meyers
*Assistant Examiner*—John W. Rollins, Jr.
*Attorney, Agent, or Firm*—Stevens, Davis, Miller & Mosher

[57] ABSTRACT

A new lipophobic fraction has been prepared by the extraction of camomile flowers with boiling ethyl or methyl alcohol, which can contain up to 30% water, letting the alcoholic solution evaporate to obtain a residue and washing the obtained residue with the appropriate organic solvents.

This fraction is particularly free of any of the camomile extract components that are volatile in steam current and the fraction has a strong bacteriostatic and bactericidal action.

Therapeutic compositions having antibacterial action were prepared, using the lipophobic fraction of the camomile extract prepared as described above.

2 Claims, 10 Drawing Figures

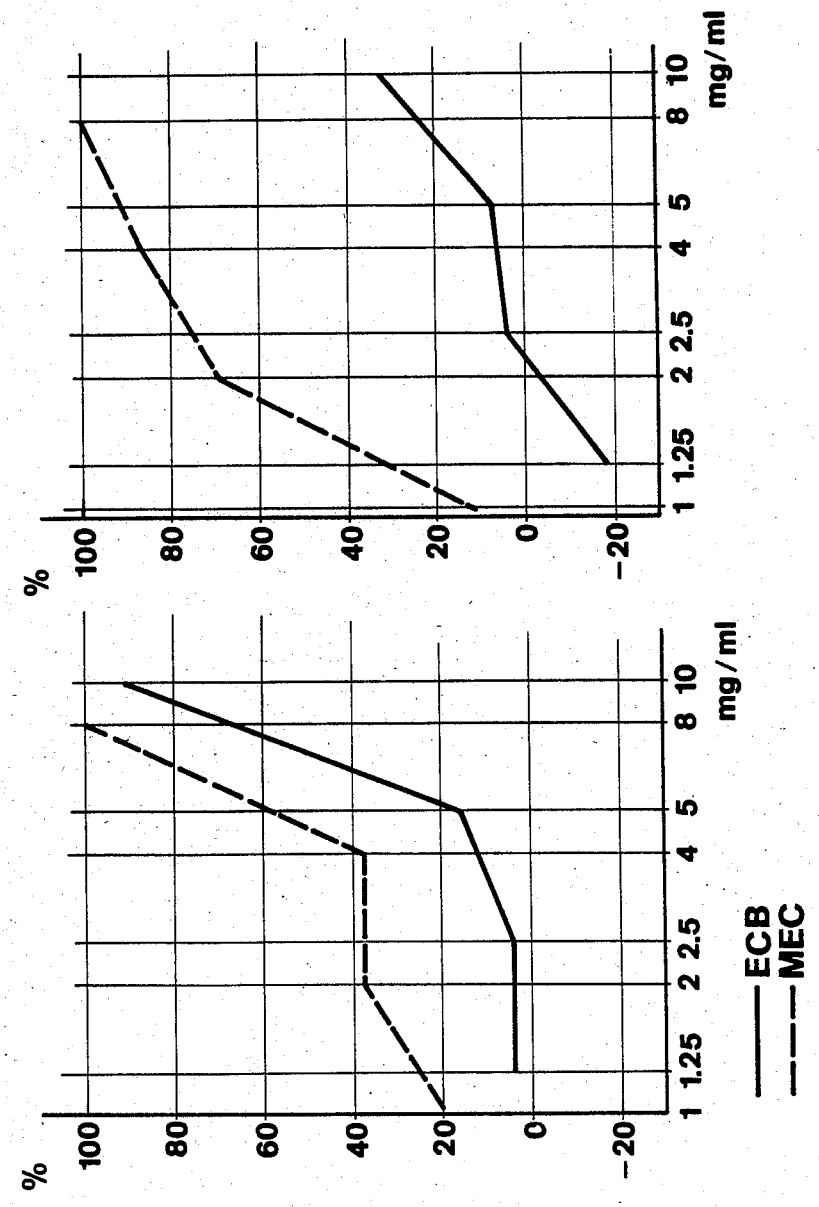

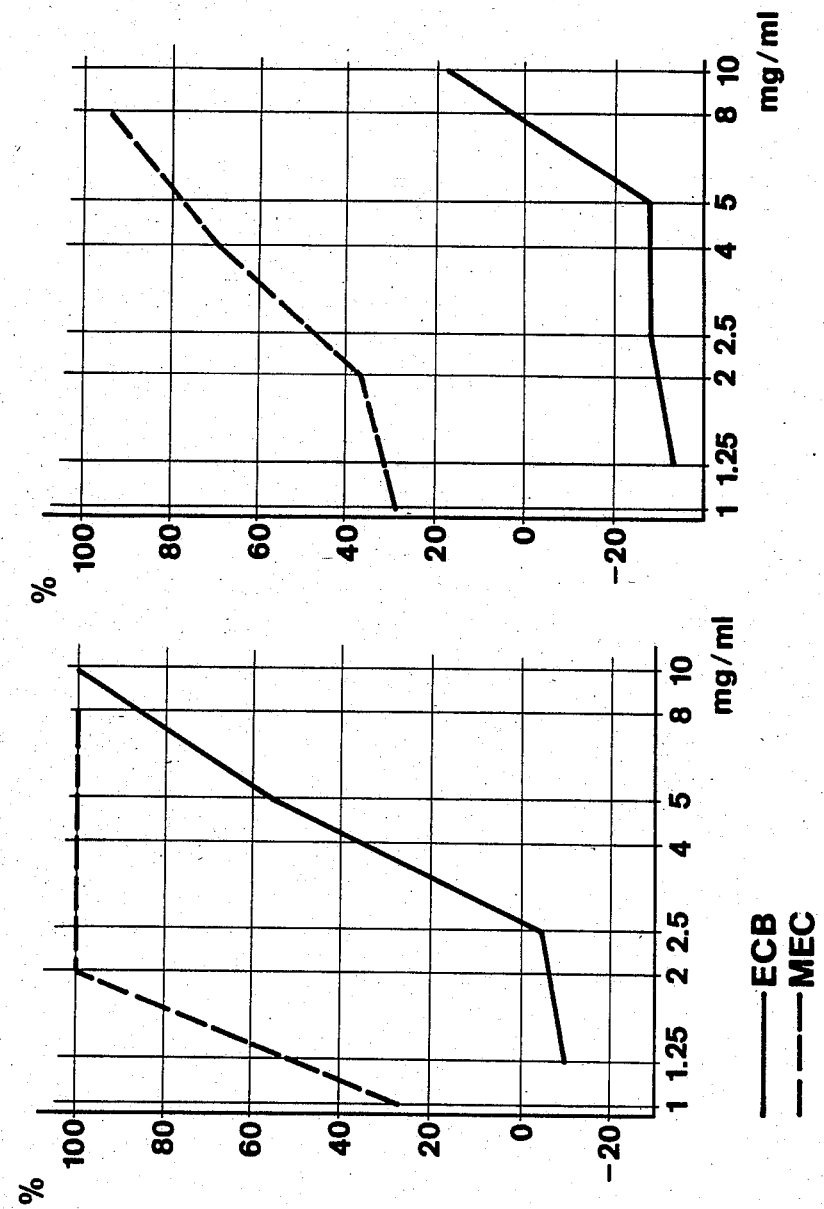

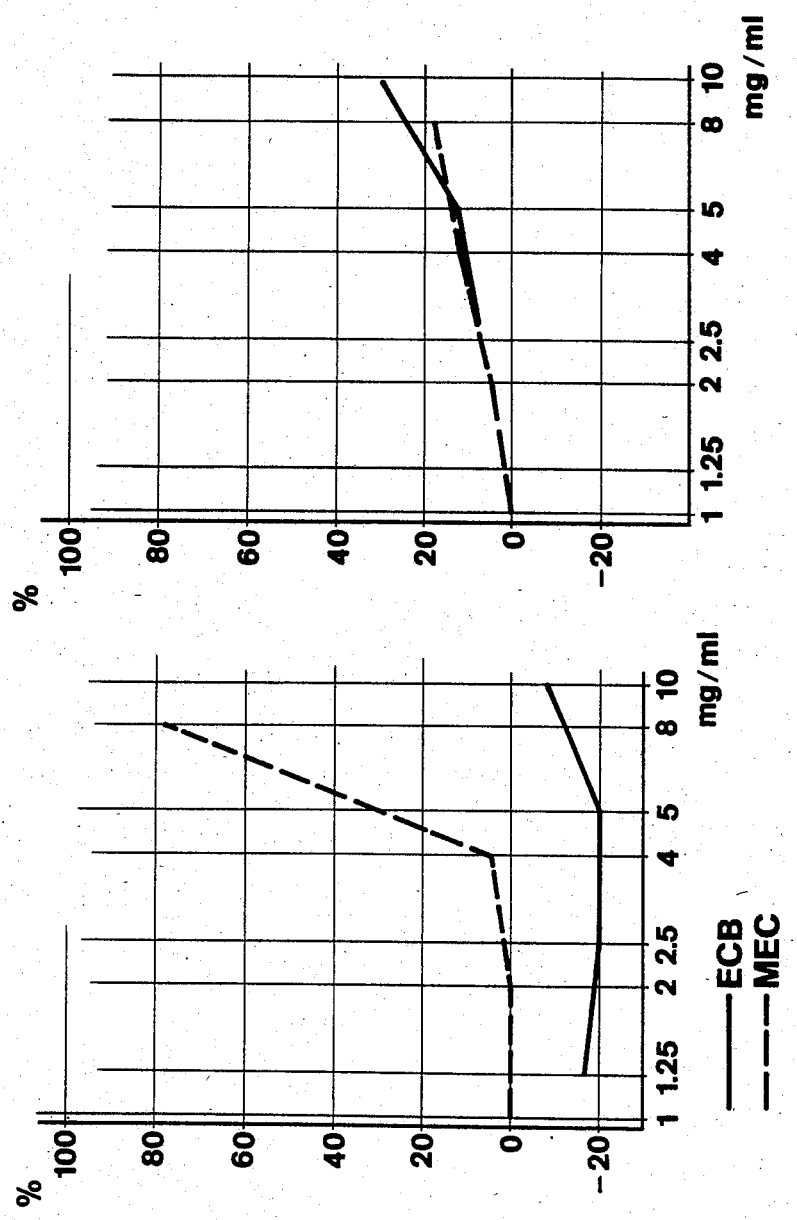

——— ECB
- - - - MEC

THERAPEUTIC COMPOSITIONS HAVING ANTIBACTERIC ACTIVITY COMPRISING A FRACTION EXTRACTED FROM CAMOMILE FLOWERS AND PROCESS FOR THE PREPARATION OF SAID FRACTION

The present invention concerns a process for the extraction of a lipophobic fraction from camomile flowers and the use of this fraction in human therapy.

More precisely, this invention concerns therapeutic compositions having marked antibacterial activity, which is selective for particular bacteria, as well as the process for extracting the fraction having the antibacterial activity from camomile flowers which fraction has to be used for the preparation of therapeutic compositions.

It is known that the camomile infusions, used as far back as ancient times for their calming and antiphlogistic action, also have a slight disinfecting action. Since the antiseptic properties of plants containing essential oils are attributed, in general, to the essential oils they contain (Tyler V. E. et al. "Pharmacognosy" VII Ed. Lea-Febiger, Philadelphia 1976, p. 137), the researchers who have investigated the slight disinfecting properties of camomile infusions have, up to now, concentrated their attention on the components that are volatile in steam current. These components were isolated and tests were carried out with the more common bacterial strains [Breinlich J. et al.—Arzneim. Forsch. 18, 429 (1968); Aggag M. E. et al.—Planta Medica 22, 140 (1972); Szalontai M. et al.—Pharm. Ztg. 120, 982 (1975); Isaac O. et al.—Med Welt. Bd. 31, 1145 (1980)].

The results of these tests, however, proved discouraging as far as making practical use of the volatile components of camomile extract as antibacterials is concerned.

We have now found, and this discovery forms the object of the present invention, that a lipophobic fraction is present in the extract of camomile containing constituents which have not yet been identified and that this fraction can be obtained in a constant and reproducible way, thus removing the lipophilic components from the total extract and among them the essential oils. This fraction has completely unexpectedly proven to have strong antibacterial activity, especially as concerns specific strains, and thus suitable for use in human and veterinary medicinal applications.

So as to permit the preparation of the camomile extract fraction, which is the object of this present invention, we give the following description of one of the preferred ways for realizing the preparation process.

EXAMPLE 1,500 grams of finely-powdered camomile flowers are extracted by refluxing in ethyl alcohol (96°) for 4 hours. The extract is filtered hot and allowed to evaporate to dryness. The pasty residue is washed several times with cold hexane under agitation.

The solid, yellow residue obtained after washing is dissolved in boiling-hot methanol and the solution is filtered. Evaporation of the methanol produces a yellow-brown solid residue weighing 330 g, which we refer to hereafter as MEC. It was determined that the fraction thus prepared is absolutely free of any volatile components (commiphoras, azulenes, dicycloethers, flavones, apigenine) and constitutes about 80% of the total, dry, hydroalcoholic extract of camomile flowers.

Along more general lines, the preparation of the camomile-flower extract requires the following:
(a) an extraction of the mass, using boiling methyl or ethyl alcohol and containing up to as much as 30% water;
(b) washing with a cold hydrocarbon solvent, preferably one pertaining to the group which consists of pentane, hexane, cyclohexane and petroleum ether;
(c) dissolving in an alcoholic solvent, preferably ethanol or methanol, to homogenize the extract, followed by new drying.

The antimicrobic activity of the MEC product was evaluated by using the standard method of serial dilution in a liquid followed by a vital count on solid terrain [Meingassner et al. Arzneim. Forsch. 31, 6 (1981)]. By this method, a Minimum Lethal Concentration (MLC) is defined, which is given by the maximum dilution whereby, after a certain period of incubation, no moving organisms are visible under the microscope, and a Minimum Inhibiting Concentration (MIC), which corresponds to the maximum dilution whereby there is no growing of the inoculated population; that is, growing is inhibited by 100%.

For the antibacterial tests, the following strains were used:

*Bacillus megatherium* ATCC 96; *Staphylococcus aureus* ATCC 12600; *Staphylococcus epidermidis*, vaginal isolation; Streptococcus, group B, vaginal isolation; *Streptococcus faecalis*, vaginal isolation; *Streptococcus mutans*, oral isolation; *Streptococcus salivarius*, oral isolation; *Pseudomonas aeruginosa* ATCC 27853; *Klebsiella pneumoniae*, vaginal isolation and *Candida albicans*; vaginal isolation.

The following graphs show growth inhibition percentage with respect to the controls after 8 hours of incubation at 37° C. Concentration of dry substance per ml of diluent is plotted on the abscissa in mg, while the percent growth inhibition is plotted on the ordinate.

The values marked with an asterisk (x) indicate the "number of bacteria below inoculation", while those marked with two asterisks (xx) indicate "bactericidal capability". For the sake of comparison, the graphs also show the data obtained with a dry, total, hydroalcoholic extract of camomile flowers, which we will hereafter refer to as ECB.

FIGS. 2, 3 and 4 refer to the tests carried out with vaginal, Gram (+) bacteria. The curves indicate precisely the following:

FIG. 1 shows the results obtained with the *Staphylococcus aureus*.

It is evident that the inhibiting action of the MEC fraction is considerably greater than the ECB extract fraction, so much so as to be therapeutically significant. While up to a concentration of 5 mg/ml the ECB has practically no action at all, the MEC fraction already gives 40% inhibition at a concentration of 2 mg/ml. 100% inhibition is then achieved at 7 mg/ml and at 8 mg/ml the number of bacteria is actually below inoculation.

FIG. 2 shows the results obtained with *Staphilococcus epidermidis*.

The ECB total extract, with this bacteria, actually has a stimulating action at the lower concentrations; that is, the growth of the bacteria is stimulated. At the higher concentrations, its inhibiting action is minimal. Under the same conditions, the MEC fraction causes 70% inhibition at 2 mg/ml concentrations and at 8 mg/ml concentrations causes a number of bacteria inferior to inoculation; that is, not only is the MIC obtained, but there is also bacterial lysis.

FIG. 3 shows the results obtained with group B Streptococcus.

The tests revealed that at the lower ECB concentrations bacterial growth was stimulated and that inhibitory action only began occurring in a measurable way at about 4 mg. The MEC fraction, on the other hand, obtained the MIC condition at concentrations of 1.5 mg/ml and, at higher concentrations, caused the disappearance, that is, lysis, of the initial inoculation bacteria.

FIG. 4 refers to the *Streptococcus faecalis* bacteria. The total extract also has a stimulating action on the growth of this bacteria for concentrations up to practically 8 mg/ml. At the 8 mg/ml concentrations, the MEC fraction reaches the MIC.

FIGS. 5, 6 and 7 refer to the tests carried out with the vaginal Gram (−) bacteria. The curves indicate precisely the following:

FIG. 5 refers to the bacteriostatic activity on the *Pseudomonas aeruginosa*.

The total ECB extract, at any concentration, has an activating effect on the growth of the bacteria. The MEC fraction never has an activating action and begins having an inhibitory action at a concentration of 4 mg/ml. The MIC is then rapidly reached at a value which is less than 8 mg/ml.

FIG. 6 shows that both the ECB and MEC have about the same negligible activity on the *Klebsiella pneumoniae* bacteria.

FIG. 7 refers to the results obtained with the *Candida albicans*.

The MEC is shown to be decidedly superior to the ECB in its inhibitory action and, above all, is not stimulating. The inhibition of 50% reached at 8 mg/ml, however, is not particularly interesting when considering a practical application.

Figure 8:
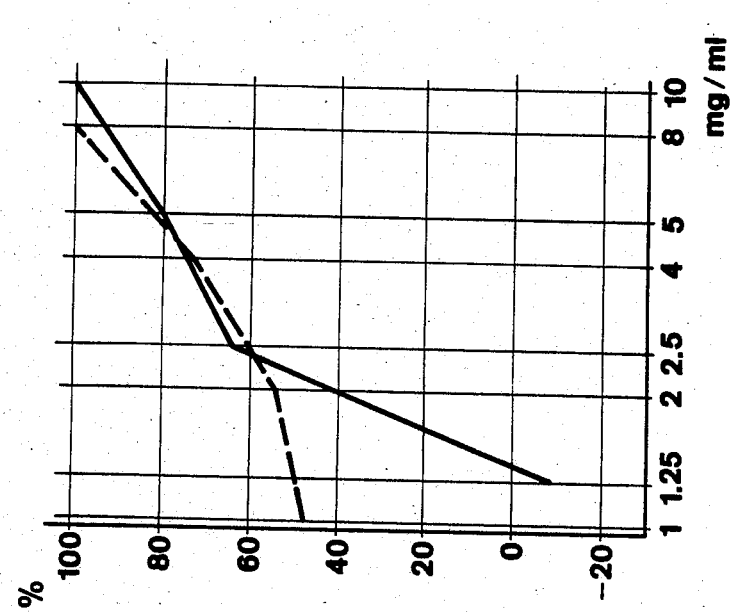
Figure 10:
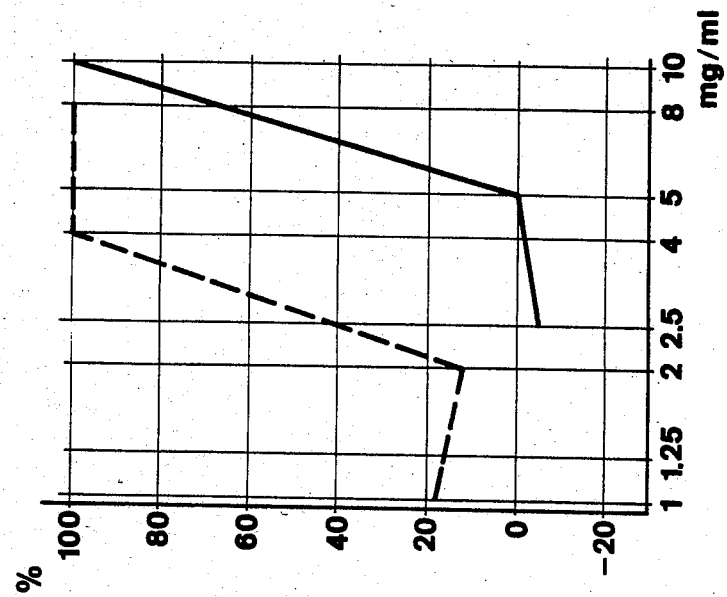
Figure 9:
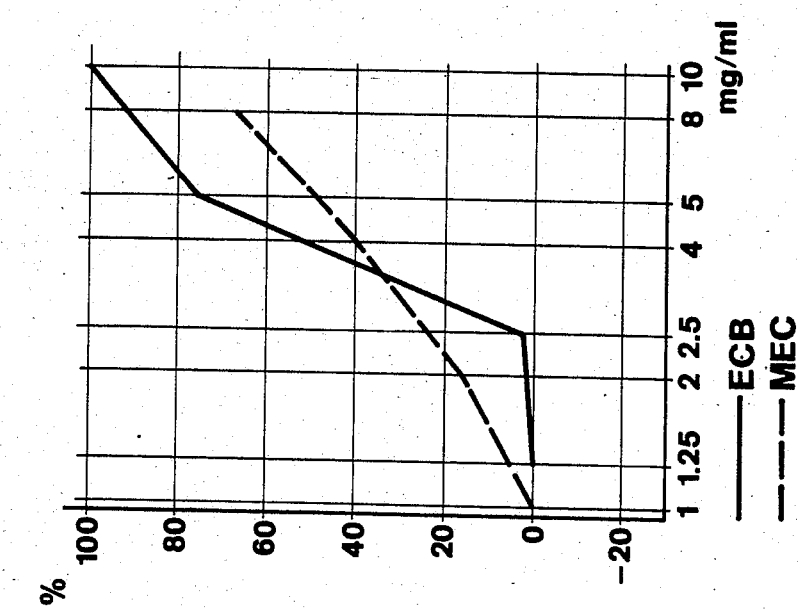

FIGS. 8 and 9 refer to the treatment of the oral Gram (+) bacteria, and FIG. 10 refers to the treatment of the sporogenous, nonpathogenic Gram (+). The curves indicate precisely the following:

FIG. 8 shows the results obtained with the *Streptococcus mutans*.

It is evident from the graphs that the MEC is very strongly inhibitory at low concentrations while the ECB is not, and also that it reaches its bactericidal strength at a concentration of about 7 mg/ml.

FIG. 9 shows that both the ECB and MEC demonstrate an activity which is not very interesting as far as the *Streptococcus salivarius* is concerned.

FIG. 10 refers to the tests carried out with the *Bacillus megatherium*.

In this case, the activity of the MEC begins at a point considerably below that of the ECB and the "bactericidal strength" of the MEC obtains at a concentration of 2.5 mg/ml, all of which makes it extremely interesting for use in therapy.

From the above described figures and accompanying comments, the following is deduced:

a—The lipophobic fraction (MEC) of the total extract of camomile flowers (ECB) has an antibacterial action which is neverless than that of the ECB, which was not logical to presume because of the essential oils fraction having been eliminated.

b—The antibacterial activity of the MEC is never negative; that is, stimulating for the bacterial strains. This is not, however, the case with the ECB.

c—On the whole, it can be said that the antibacterial action characteristics of the MEC are completely independent of those of the ECB and cannot be at all foreseen or predicted by referring to the ECB. Furthermore, there is no logical explanation for the fact that while the ECB is only blandly anticeptic and cannot, certainly, be utilized in a chemiotherapeutic product and also that steam-current volatile fractions and the single products which constitute it also have only a moderate effect in controlling certain bacteria—an effect of practically no medical import, the lipophobic fraction which has been isolated from the total camomile extract, for the first time, shows a strong bacteriostatic and bactericidal action which is utilizable both in human and veterinary therapy;

d—The activity of the MEC on certain bacteria is particularly high, which makes it utilizable for the preparation of pharmaceutical products having selective antibacterial activity.

e—It is obvious that the new pharmaceutical has no toxic or other side effects.

As it has already been mentioned, the new antibacterial product, according to this present invention, can be used in either the dry state or mixed with standard diluents or solvents or appropriately selected excipients commonly used in medicine.

We claim:

1. A pharmaceutical composition useful for treating bacterial infections in humans and animals which comprises an antibacterially effective amount of the lipophobic fraction of an alcoholic extract of camomile flowers in combination with a pharmaceutically acceptable carrier, said lipophobic fraction being obtained by:

(a) extracting the flowers with methyl or ethyl alcohol at boiling temperature of the alcohol, the alcohol containing not more than 30 percent water;

(b) washing the alcoholic extract with a cold hydrocarbon solvent selected from the group consisting of pentane, hexane, cyclohexane and petroleum ether;

(c) drying the washed alcoholic extract and dissolving the dired residue in ethyl or methyl alcohol to form a solution, filtering the solution and then evaporating the solution to obtain a final solid product.

2. The pharmaceutical composition of claim 1 in which the alcohol used in the extraction step is 96 percent ethyl alcohol and the hydrocarbon solvent used in the washing step is hexane.

* * * * *